(12) United States Patent
Trese

(10) Patent No.: US 6,428,553 B1
(45) Date of Patent: Aug. 6, 2002

(54) ILLUMINATED OPHTHALMIC MEMBRANE PICK ASSEMBLY

(75) Inventor: Michael T. Trese, Bloomfield Hills, MI (US)

(73) Assignee: NuVue Technologies, Inc., Keene, NH (US)

(*) Notice: Subject to any disclaimer, the term of this patent is extended or adjusted under 35 U.S.C. 154(b) by 0 days.

(21) Appl. No.: 09/520,913

(22) Filed: Mar. 8, 2000

(51) Int. Cl.[7] ................................................ A61B 17/36
(52) U.S. Cl. .......................................... 606/161; 606/16
(58) Field of Search ............................ 606/1, 161, 166, 606/170, 2, 4, 6, 174, 15, 16; 604/117, 21, 20, 289, 294; 600/104, 166, 177, 182

(56) References Cited

U.S. PATENT DOCUMENTS

| | | | |
|---|---|---|---|
| 4,878,487 A | * | 11/1989 | Sinnett |
| 5,078,712 A | * | 1/1992 | Easley et al. .................. 606/16 |
| 5,554,155 A | * | 9/1996 | Awh et al. ..................... 606/16 |
| 5,725,514 A | * | 3/1998 | Grinblat et al. ............... 606/15 |

* cited by examiner

Primary Examiner—David O. Reip
(74) Attorney, Agent, or Firm—Gifford, Krass, Groh, Sprinkle, Anderson & Citkowski, P.C.

(57) ABSTRACT

An illuminated ophthalmic membrane pick assembly is disclosed having an elongated housing and a throughbore extending between the housing ends. An elongated tubular probe has one end secured to one end of the housing in alignment with the housing throughbore. A membrane pick is secured to the other or free end of the probe so that a free end of the membrane pick overlies the free end of the probe. An optical fiber is longitudinally slidably disposed through the housing throughbore and the probe while a button mechanically secured to the optical fiber and slidably mounted to the housing moves the optical fiber between an extended and a retracted position. In its extended position, the optical fiber laterally outwardly displaces the membrane pick so that the free end of the pick abuts against a side of the optical fiber. Conversely, in its retracted position, the optical fiber is nested within the probe.

8 Claims, 2 Drawing Sheets

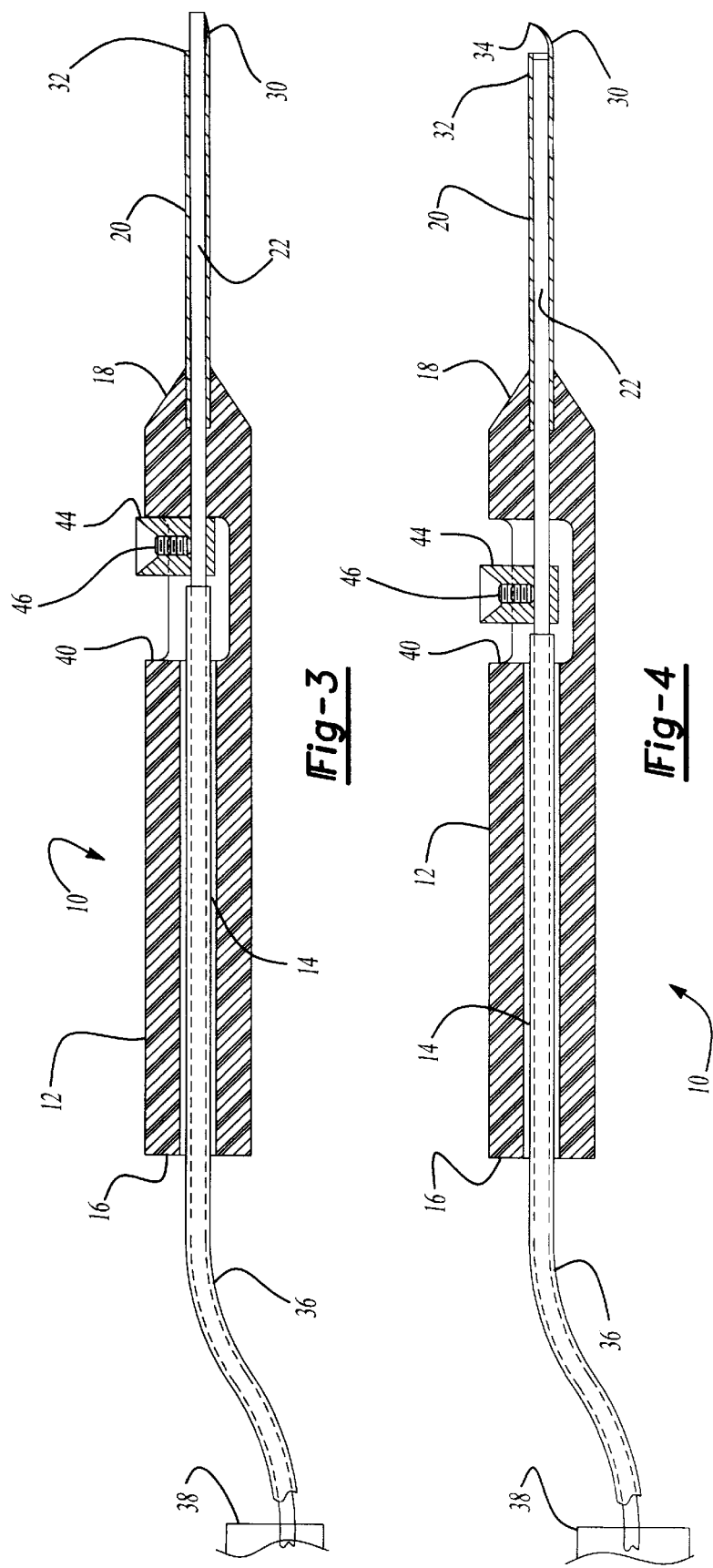

ILLUMINATED OPHTHALMIC MEMBRANE PICK ASSEMBLY

BACKGROUND OF THE INVENTION

I. Field of the Invention

The present invention relates generally to medical instruments and, more particularly, to an illuminated ophthalmic membrane pick assembly.

II. Description of the Prior Art

Ophthalmic surgery usually requires the introduction of instruments into the interior of the eyeball. An opening is formed in the eyeball and sometimes a cannula is inserted into the opening. Thereafter, instruments are inserted through the eye opening so that an end of the instrument is within the interior of the eyeball.

In many types of ophthalmic surgery it is necessary to simultaneously insert multiple medical instruments into the interior of the eyeball. In many instances, each instrument requires its own scleral opening and own cannula although combination instruments have been previously known.

One such type of combination instrument comprises an illuminated membrane pick. These previously known illuminated membrane picks typically comprise an elongated housing adapted to be manually manipulated by the surgeon. A probe extends outwardly from one end of the housing and is dimensioned for insertion through a cannula positioned through the sclera. A membrane pick is then secured to the free or distal end of the probe while an optical fiber mounted within the probe provides illumination in the interior of the eye.

One disadvantage of this previously known illuminated membrane pick is that the membrane pick is always in an exposed and operable position once positioned within the eye. The pick is commonly used to dissect membranes, remove layers of scar tissue and the like. One disadvantage of these previously known illuminated membrane picks, however, is that since the pick is always in an exposed and operable position, movement of the pick within the interior of the eye can result in unintentional damage and iatrogenic openings in the eye. In some cases, the membrane pick even damages the sclera as the pick is inserted through and removed from the cannula.

SUMMARY OF THE PRESENT INVENTION

The present invention provides an illuminated ophthalmic membrane pick which overcomes all of the above-mentioned disadvantages of the previously known devices.

In brief, the assembly of the present invention comprises an elongated housing having a longitudinally extending throughbore. An elongated tubular probe has one end secured to the housing in alignment with the housing throughbore and this probe is dimensioned for insertion through a cannula into the interior of an eyeball. A membrane pick is fixedly secured to the free or distal end of the probe so that the free end of the membrane pick overlies the free end of the probe.

An elongated optical fiber is longitudinally slidably disposed through both the housing throughbore and the probe. A button is then slidably mounted to the housing and mechanically fixed to the optical fiber so that the button and optical fiber move in unison with each other.

The button is operable to move the optical fiber between a retracted position and an extended position. In its extended position, an end of the optical fiber protrudes outwardly from the probe and laterally or radially outwardly displaces the free end of the membrane pick such that the free end of the membrane pick is nested against the side of the optical fiber. Conversely, in its retracted position, the optical fiber is nested within the interior of the probe.

In its extended position, the optical fiber effectively shields eye tissue from the membrane pick to prevent damage to the eye during movement of the pick within the interior of the eye. While in its extended position, the optical fiber is fully operational and provides illumination to the interior of the eyeball.

Conversely, in its retracted position, the end of the optical fiber is retracted away from the optical pick such that the optical pick overlies the free end of the probe and is in an exposed and operable position for membrane dissection and other medical procedures. While in its retracted position, however, the optical fiber continues to provide illumination from a light source to the interior of the eye.

BRIEF DESCRIPTION OF THE DRAWING

A better understanding of the present invention will be had upon reference to the following detailed description, when read in conjunction with the accompanying drawing, wherein like reference characters refer to like parts throughout the several views, and in which:

FIG. 3 is a side view illustrating the optical fiber in an extended position;

FIG. 4 is a side view similar to FIG. 2 but illustrating the optical fiber in a retracted position;

DETAILED DESCRIPTION OF A PREFERRED EMBODIMENT OF THE PRESENT INVENTION

With reference first to FIGS. 1–4, a preferred embodiment of the illuminated ophthalmic membrane pick assembly 10 of the present invention is there shown and comprises an elongated housing 12 dimensioned to be hand held and manipulated by an eye surgeon. The housing 12 includes an elongated throughbore 14 (FIGS. 3 and 4) which extends between opposed longitudinal ends 16 and 18 of the housing 12.

Figure 1:
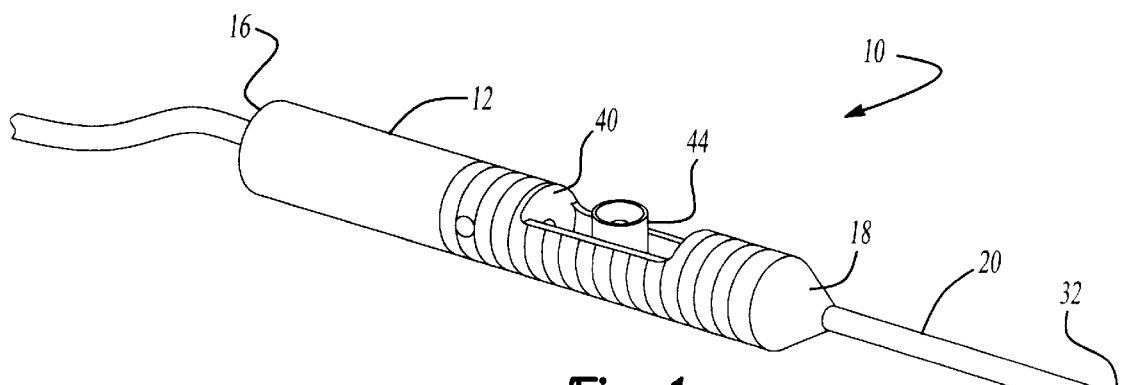
FIG. 1 is a perspective view illustrating a preferred embodiment of the present invention.
Figure 2:
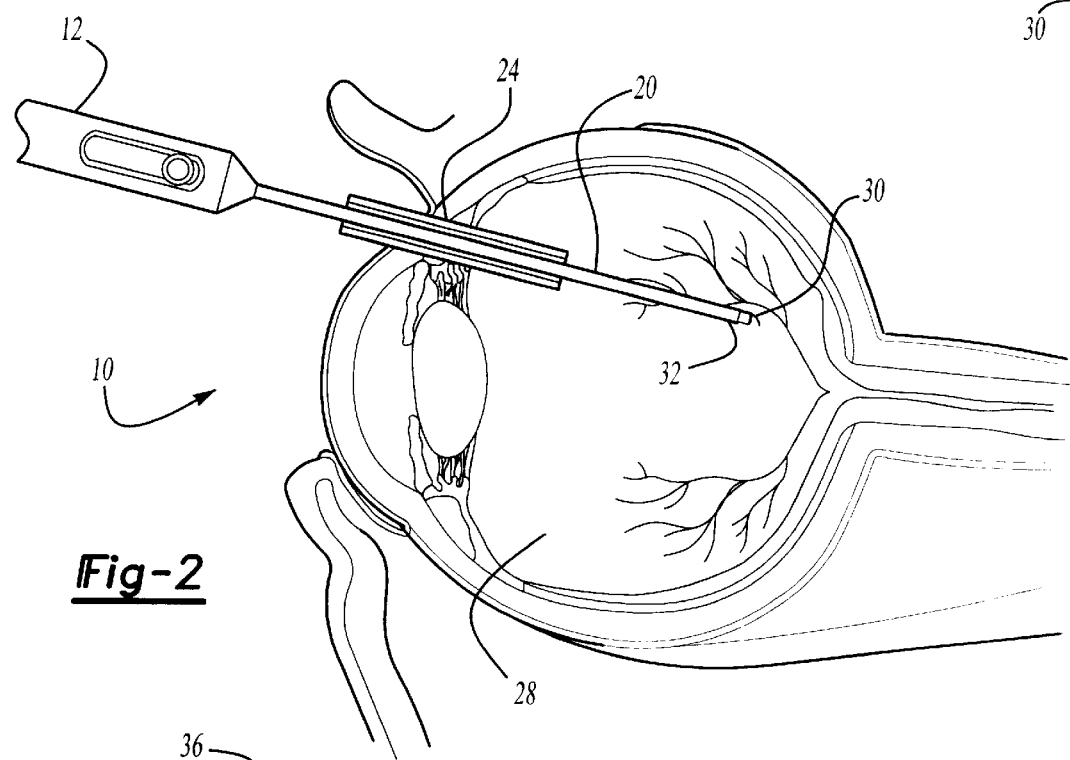
FIG. 2 is a perspective view illustrating the invention in use in an eyeball.

An elongated tubular and cylindrical probe 20 is fixedly secured to the end 18 of the housing 12 so that an internal bore 22 of the probe 20 registers with the housing throughbore 14. The probe 20 is dimensioned for insertion through a cannula 24 (FIG. 2) into the interior 26 of an eyeball 28 (FIG. 2).

A membrane pick 30 is fixedly secured to the free or distal end 32 of the probe 20 so that a free end 34 (FIG. 4) of the membrane pick 30 overlies the free end 32 of the probe 20. The membrane pick 34 is constructed of any conventional material, typically a titanium alloy, and once inserted into the interior 26 of the eyeball 28, the membrane pick 34 is used to dissect layers of membranes, scar tissue or the like from the interior of the eyeball 28.

With reference now to FIGS. 3 and 4, an elongated optical fiber 36 is longitudinally slidably disposed through the housing throughbore 14 and the bore 22 of the probe 20. One end of the optical fiber 36 is connected in any conventional fashion to a conventional light source 38 (illustrated diagrammatically).

The housing 12 includes a longitudinally extending slot 40 along an intermediate portion of the housing 12. This slot 40 is open to both the throughbore 14 as well as an exterior surface 42 of the housing 12. A button 44 is longitudinally slidably disposed in the slot 40 and is mechanically connected to the optical fiber 36 in any conventional way, such as by a fastener 46, so that the button 44 and optical fiber 36 move in unison with each other.

Figure 5:
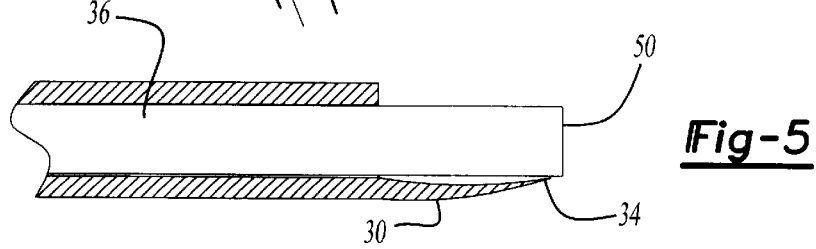
FIG. 5 is an enlarged fragmentary view illustrating the optical fiber in an extended position.
Figure 6:
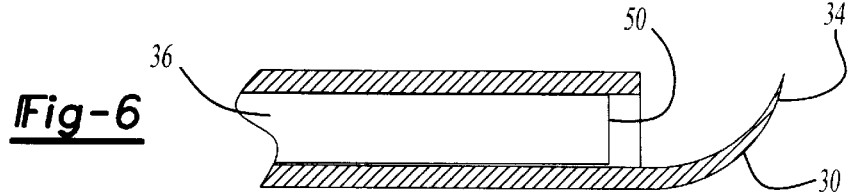
FIG. 6 is a view similar to FIG. 5, but illustrating the optical fiber in a retracted position.

The button 44 is utilized to move the optical fiber between a retracted position, illustrated in FIGS. 4 and 5, and an extended position, illustrated in FIGS. 3 and 6. As best shown in FIGS. 5 and 6, when the button 44 is used to move the optical fiber 36 to its extended position, a free end 50 of the optical fiber 36 laterally deflects the free end 34 of the membrane pick 30 laterally or radially outwardly such that the free end 34 of the membrane pick 30 abuts against the side of the optical fiber 36 closely adjacent the free end 50 of the optical fiber 36. Thus, with the optical fiber 36 in its extended position, the optical fiber effectively shields eye tissue from the free end 34 of the membrane pick 30 to prevent unintended damage to the eye tissue from the membrane pick 30 during movement of the membrane pick assembly 10. When the optical fiber 36 is in its extended position, the end 50 of the optical fiber 36 can also be used as a blunt ophthalmic instrument.

Conversely, with the optical fiber 36 in its retracted position (FIG. 6), the free end 50 of the optical fiber 36 is nested within the interior of the probe 20. In this position, the membrane pick 30, due to its shape memory, returns to its original shape and position overlying the end 32 of the probe 20 and thus in an exposed and operable position. Furthermore, regardless of whether the optical fiber 36 is in its extended or retracted position, the optical fiber 36 can be used to provide illumination to the interior of the eyeball.

From the foregoing, it can be seen that the present invention provides a unique and novel illuminated ophthalmic membrane pick assembly. Having described my invention, however, many modifications thereto will become apparent to those skilled in the art to which it pertains without deviation from the spirit of the invention as defined by the scope of the appended claims.

I claim:

1. An illuminated ophthalmic pick assembly comprising:
   a housing having two ends and a throughbore extending between said housing ends,
   an elongated tubular probe having two ends, one end of said probe being secured to one end of the housing in alignment with said housing throughbore,
   a membrane pick secured to the other end of said probe so that a free end of said membrane pick overlies the other end of said probe,
   an optical fiber longitudinally slidably disposed through said housing throughbore and said probe,
   means for manually moving said optical fiber relative to said probe between a retracted position in which one end of said optical fiber is retracted from said membrane pick, and an extended position in which said one end of said optical fiber displaces said free end of said membrane pick laterally outwardly from the other end of said probe, said free end of said membrane pick abutting against a side of said optical fiber when said optical fiber is in said extended position.

2. The invention as defined in claim 1 wherein said housing is elongated, said housing throughbore extending longitudinally through said housing.

3. The invention as defined in claim 2 wherein said housing includes a slot extending longitudinally along an intermediate portion of said housing, said slot being open to both said housing throughbore and an outside surface of said housing, and wherein said moving means comprises a button longitudinally slidably mounted in said slot, said button being mechanically secured to said optical fiber.

4. The invention as defined in claim 1 and comprising a light source and means for attaching the other end of said optical fiber to said light source.

5. The invention as defined in claim 1 wherein with said optical fiber in said retracted position, said one end of said optical fiber is nested within said probe.

6. The invention as defined in claim 5 wherein with said optical fiber in said retracted position, said one end of said optical fiber is substantially flush with the other end of said probe.

7. An illuminated ophthalmic pick assembly comprising:
   a housing having two ends and a throughbore extending between said housing ends,
   an elongated tubular probe having two ends, one end of said probe being secured to one end of the housing in alignment with said housing throughbore,
   a membrane pick secured to the other end of said probe so that a free end of said membrane pick overlies the other end of said probe,
   an optical fiber longitudinally slidably disposed through said housing throughbore and said probe,
   means for moving said optical fiber between a retracted position in which one end of said optical fiber is retracted from said membrane pick, and an extended position in which said one end of said optical fiber displaces said free end of said membrane pick laterally outwardly from the other end of said probe,
   wherein said housing is elongated, said housing throughbore extending longitudinally through said housing, and
   wherein said housing includes a slot extending longitudinally along an intermediate portion of said housing, said slot being open to both said housing throughbore and an outside surface of said housing, and wherein said moving means comprises a button longitudinally slidably mounted in said slot, said button being mechanically secured to said optical fiber.

8. An illuminated ophthalmic pick assembly comprising:
   a housing having two ends and a throughbore extending between said housing ends,
   an elongated tubular probe having two ends, one end of said probe being secured to one end of the housing in alignment with said housing throughbore,
   a membrane pick secured to the other end of said probe so that a free end of said membrane pick overlies the other end of said probe,
   an optical fiber longitudinally slidably disposed through said housing throughbore and said probe,
   a button mechanically secured to said optical fiber and longitudinally slidably mounted to said housing between a retracted position in which one end of said optical fiber is retracted from said membrane pick, and an extended position in which said one end of said optical fiber displaces said free end of said membrane pick laterally outwardly from the other end of said probe.

* * * * *